United States Patent [19]

Orban et al.

[11] Patent Number: 5,726,310
[45] Date of Patent: Mar. 10, 1998

[54] PROCESS FOR THE PREPARATION OF 2-(2, 4-DIHYDROXYLPHENYL)-4,6-BIS(2,4-DIMEHYLPHENYL)-S-TRIAZINE

[75] Inventors: Ivan Orban, Basel; Martin Holer, Magden; André Kaufmann, Lampenberg, all of Switzerland

[73] Assignee: Ciba Specialty Chemicals Corporation, Tarrytown, N.Y.

[21] Appl. No.: 758,316

[22] Filed: Dec. 3, 1996

[51] Int. Cl.$^6$ ............................................. C07D 251/24
[52] U.S. Cl. ............................................................ 544/216
[58] Field of Search ............................................. 544/216

[56] References Cited

U.S. PATENT DOCUMENTS

| | | | |
|---|---|---|---|
| 3,244,708 | 4/1966 | Duenssenberger | 260/248 |
| 3,268,474 | 8/1966 | Handy et al. | 260/45.8 |
| 4,092,466 | 5/1978 | Fletcher | 526/13 |

FOREIGN PATENT DOCUMENTS 884802 12/1961 United Kingdom.

OTHER PUBLICATIONS

Helv. Chim Acta 33, 1365 (1950) Hirt et al.
Helv. Chim Acta 55, 1575, 1589 (1972).

*Primary Examiner*—John M. Ford
*Attorney, Agent, or Firm*—Luther A. R. Hall

[57] ABSTRACT

2-(2,4-Dihydroxyphenyl)-4,6-bis(2,4-dimethylphenyl)-s-triazine is prepared by reacting cyanuric chloride with m-xylene at a temperature of 0°–110° C. in the presence of a Lewis acid and at least one inert chlorinated aromatic solvent to give the intermediate 2-chloro-4,6-bis(2,4-dimethylphenyl)-s-triazine. This intermediate, without being isolated, is then reacted with resorcinol to give the final desired product 2-(2,4-dihydroxyphenyl)-4,6-bis(2,4-dimethylphenyl)-s-triazine in good yield.

13 Claims, No Drawings

PROCESS FOR THE PREPARATION OF 2-(2, 4-DIHYDROXYLPHENYL)-4,6-BIS(2,4-DIMEHYLPHENYL)-S-TRIAZINE

Process for the Preparation of 2-(2,4-dihydroxyphenyl)-4,6-bis(2,4-dimethylphenyl)-s-triazine The present invention relates to a novel, simplified and thus more economical process for the preparation of 2-(2,4-dihydroxyphenyl)-4,6-bis(2,4-dimethylphenyl)-s-triazine from cyanuric chloride.

The reaction of cyanuric chloride with 1,3-xylene under Friedel-Crafts conditions to give 2-chloro-4,6-bis(2,4-dimethylphenyl)-s-triazine is known, e.g. from DE-A-1 169 947 and Helv. Chim. Acta 55, 1589 (1972). However, the product can also be obtained using an appropriate Grignard reagent, such as described in Helv. Chim. Acta 33, 1365 (1950) and U.S. Pat. No. 4,092,466.

The further reaction of the 2-chloro-4,6-bis(2,4-dimethylphenyl)-s-triazine, which is purified beforehand by recrystallisation, with resorcinol is described in U.S. Pat. No. 3,244,708.

The direct reaction of cyanuric chloride with two equivalents of 1,3-xylene, however, has the disadvantage that mono- and trisubstituted products are additionally formed. In particular, the mono-xylyl derivative is undesirable, as it leads in the subsequent stage with resorcinol to the corresponding bis-resorcinol compound. The latter can lead to yellowing in the use of the UV absorbers prepared from the compound of the formula I in various polymer substrates, e.g. in certain lacquers. The formation of this bis-resorcinol compound was earlier excluded by means of the circuitous dichloroalkoxy-s-triazine route (Helv. Chim. Acta 55, 1575 (1972)).

It has now been found that 2-(2,4-dihydroxyphenyl)-4,6-bis(2,4-dimethylphenyl)-s-triazine can be prepared by reaction of cyanuric chloride with 1,3-xylene in the presence of a Lewis acid and of an inert chlorinated aromatic solvent without isolation of the chloro-s-triazine intermediate by subsequent reaction with resorcinol in the so-called one-pot process; in this process, surprisingly without increase in the tris content, virtually no monoaryl-substituted dichloro-s-triazine compound is formed in the first reaction step.

Furthermore, it was possible by means of the reaction procedure to exclude an uncontrolled exothermic reaction, which can occur on the simultaneous introduction of the starting materials and the catalyst (for this see DE-A-1 169 947 or BP 884 802), and the safety risk associated therewith.

As solvent, neither the compound of the formula III itself nor carbon disulfide (Helv. Chim. Acta 55, 1589 (1972)) is used, and the reaction mixture also does not become solid, as is described in DE-A-1 169 947.

The invention therefore provides a process for the preparation of 2-(2,4-dihydroxyphenyl)-4,6-bis(2,4-dimethylphenyl)-s-triazine of the formula I

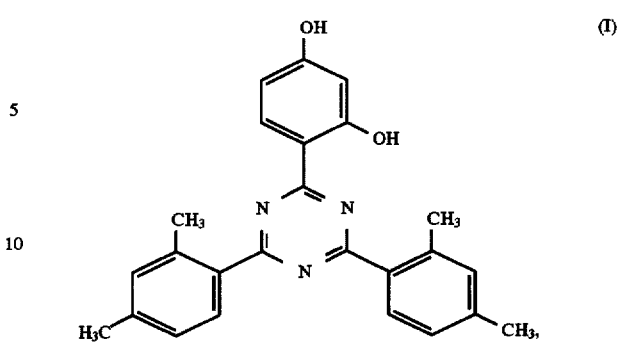

which comprises
a) reacting cyanuric chloride of the formula II

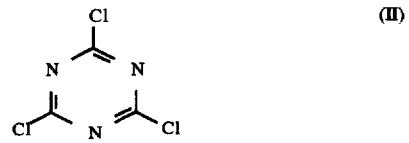

at a temperature of 0° to 110° C. in the presence of a Lewis acid in a ratio of 2.3 to 3.0 mol of Lewis acid per mole of cyanuric chloride employed in the presence of at least one inert chlorinated aromatic solvent, with 1,3-xylene of the formula III

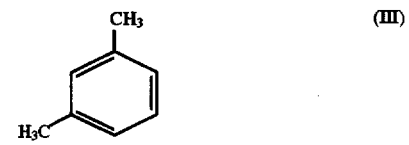

in a ratio of 2.1 to 2.5 mol of compound of the formula III per mole of cyanuric chloride employed with addition of compound of the formula III in a period of from 5 to 30 hours to give the compound of the formula IV

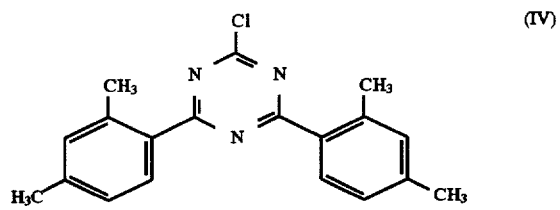

and then
b) without isolating the compound of the formula IV obtained reacting this with resorcinol in a ratio of 0.5 to 1.0 mole of resorcinol per mole of cyanuric chloride employed at a temperature from 0° to 100° C. to give the compound of the formula I.

The reaction procedure in process step a) is preferably carried out such that the compound of the formula III is added in 2 portions. Expediently, first 0.5 to 1.1 mol and then 2.0 to 1.0 mol of the compound of the formula III are added. The addition of the first portion is carried out at 60° to 110° C., in particular 75° to 95° C., that of the second at 20° to 50° C., in particular 30° to 40° C. In a particularly expedient manner, first 0.5 to 1.0 mol of the compound of the formula III are added at 60° to 110° C. to the compound of the formula II in a period of 2 to 12 hours, while the second portion of the compound of the formula III is 2.0 to 1.0 mol and is metered in at 20° to 50° C. in a period of 5 to 15 hours. The cooling phase between the two temperature ranges in this case has a length of time of ≤3 hours, for example 0.1 to 3 hours, in particular 0.5 to 2.5 hours.

In a particularly preferred manner, the reaction procedure in process step a) is carried out such that the addition of 0.85 to 1.0 mol of the compound of the formula III takes place at 83° to 87° C. in the course of 3.5 to 4.5 hours, then the mixture is cooled to 33° to 37° C. for 1.4 to 1.6 hours, after which the addition of 1.45 to 1.3 mol of the compound of the formula III takes place in the temperature range from 33° to 37° C. in the course of 5.5 to 6.5 hours.

In reaction stage a), an aromatic solvent or a mixture is employed. Examples therefor are mono-, di- or trichlorobenzene or mixtures thereof, in particular chlorobenzene or dichlorobenzene, e.g. 1,2-dichlorobenzene.

In the second reaction stage b), a different solvent from the first reaction stage a) can be used.

Suitable solvents are, for example: nitrobenzene, anisole, chlorobenzene and 1,2-dichlorobenzene or mixtures of these with one another.

If in the second reaction stage b) another solvent is used, the first solvent can be partially or completely removed, e.g. by distilling off.

Preferably, however, a chlorinated aromatic solvent is also employed in reaction stage b), in particular the same one as in reaction stage a).

In reaction stage a), the Lewis acid used in the reaction known to the person skilled in the art as a Friedel-Crafts reaction is preferably aluminium chloride or aluminium bromide, where the former is to be particularly preferred. The Lewis acids mentioned are expediently essentially anhydrous.

The Lewis acid is preferably employed in a ratio of 2.4 to 2.6 mol per mole of cyanuric chloride.

Process step b) can expediently follow directly without isolation of the product of the formula IV formed in the first process step a), i.e. working-up is unnecessary under the reaction conditions mentioned here, as in process step a) virtually no mono-xylyl compound is formed. The relatively high percentage proportion of the tris-xylyl compound does not interfere with the further course of the reaction, as this compound remains in solution during the isolation of the desired product and is therefore recovered in the filtrate. In process step b), preferably 0.7 to 0.8 mol of resorcinol are employed per mole of cyanuric chloride and the temperature during the reaction is expediently continuously increased from 35° to 80° C.

The isolation of the final product can be carried out by methods which are customary per se.

Expediently the Lewis acid is first hydrolysed.

If, for example, a chlorinated aromatic solvent is used, the compound of the formula I can be obtained as a crystalline compound by slow addition of a non-polar solvent and seeding. The temperature during the crystallization is expediently lowered and the product obtained is preferably isolated using a suction filter.

The product separated off from the solvent is expediently washed on the suction filter and then dried, drying preferably taking place in vacuo at 65° to 70° C.

The compound of the formula I is itself already distinguished by its photostabilizing action in organic materials; it can moreover be advantageously employed by substitution of the hydrogen of the p-hydroxy function for the preparation of compounds such as 2-(2-hydroxy-4-alkoxyphenyl)-4,6-bis(2,4-dimethylphenyl)-s-triazines, which are known as photostabilizers for organic material, in particular synthetic polymers. Examples of these uses of compounds similar to the formula I are found, for example, in U.S. Pat. No. 3,268,474.

The invention also provides a process for the preparation of the intermediate occurring in the process described above, of the formula IV

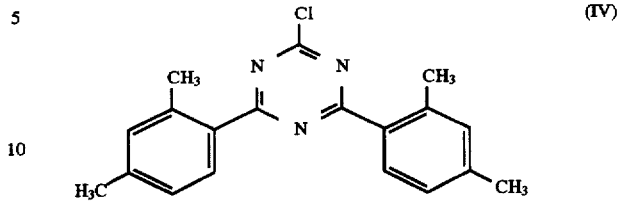

wherein cyanuric chloride of the formula II

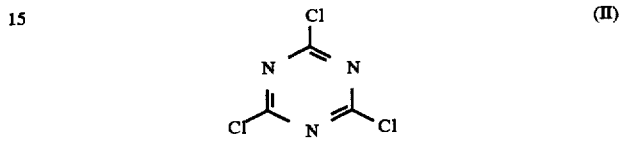

is reacted at a temperature of 0° to 110° C. in the presence of a Lewis acid in a ratio of 2.3 to 3.0 mol of Lewis acid per mole of cyanuric chloride employed in the presence of at least one inert chlorinated aromatic solvent, with 1,3-xylene of the formula III

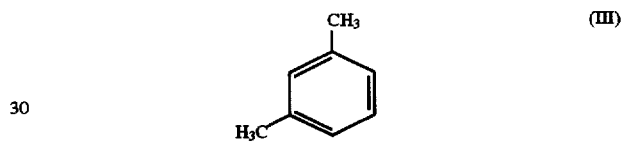

in a ratio of 2.1 to 2.5 mol of compound of the formula III per mole of cyanuric chloride employed with addition of compound of the formula III in a period of 5 to 30 hours to give the compound of the formula IV, and the compound of the formula IV obtained is isolated.

The process measures and the preferred process embodiments correspond to those described above for reaction stage a) of the one-pot process according to the invention. The isolation of the compound of the formula IV is carried out by processes known to the person skilled in the art, such as distillation of the solvent, crystallization by addition of a suitable solvent etc.

The following Example illustrates the process according to the invention further. All data in percentages are by weight, unless stated otherwise.

EXAMPLE

Preparation of 2-(2,4-dihydroxyphenyl)-4,6-bis(2,4-dimethylphenyl)-s-triazine

Process step a)

200 g (1.50 mol) of aluminium chloride are added to 110.7 g (0.60 mol) of cyanuric chloride, dissolved in 360 g of 1,2-dichlorobenzene, with stirring (about 200 rpm). The readily stirrable suspension is then heated to 84° to 86° C. in the course of 30 minutes and kept at this temperature for 15 minutes. At about 200 rpm, 67.9 ml (58.6 g, 0.55 mol) of m-xylene are metered in at 84° to 86° C. in the course of 4 hours (exothermic reaction!), then the suspension is cooled as evenly as possible to 34° to 36° C. in the course of 1.5 hours. The addition of a further 101.8 ml (87.95 g, 0.83 mol) of m-xylene is carried out at 34° to 36° C. (exothermic reaction!) in a period of 6 hours. Shortly before the end of addition, a little HCl gas is released, which is neutralized by means of NaOH (40%). After addition of xylene is complete, the readily stirrable dark-brown reaction mixture is additionally stirred at 34° to 36° C. for a further 15 minutes.

Process step b)

9.9 g (0.09 mol) of resorcinol are metered into the above reaction solution in the course of 1 hour; the temperature is furthermore 34° to 36° C. The next 9.9 g of resorcinol are likewise added in the course of 1 hour; during the course of this the temperature is increased from 35° to 48° C. A further 29.7 g of resorcinol (0.45 mol) are added at 48° C. in the course of 3 hours.

The reaction mixture is then heated to 79° to 81 ° C. in a period of 3 hours and additionally stirred at this temperature for 1 hour. The HCl gas released over the entire reaction period is neutralized by means of 40% sodium hydroxide solution.

For working-up, the above warm reaction solution is added to a solution stirred at 300 to 350 rpm, of 750 g of water and 750 g of methyl isobutyl ketone or methyl ethyl ketone which is at room temperature, in the course of 10 to 15 minutes. The product is extracted by stirring at 68° to 70° C. for 10 minutes. After phase separation, the lower (aqueous) phase is separated off and the upper organic phase is treated with 375 g of 3% hydrochloric acid. The mixture is again stirred at 68° to 70° C. for 10 minutes and after phase separation has taken place the lower (aqueous) phase is removed.

The solvents are removed from the organic phase at temperatures from about 104° to 130° C. and initial normal pressure up to 150–155 mbar at the end. 400 g of 1,2-dichlorobenzene are added to the distillation residue such that the temperature does not fall below 120° C. 580 g of heptane isomer mixture are then metered in in the course of 1 hour such that a distinct reflux always takes place. After about 200 g of heptane have been added, the solution is continuously seeded (1 g of 2-(2,4-dihydroxyphenyl)-4,6-bis(2,4-dimethylphenyl)-s-triazine in 20 g of heptane). After approximately 50% of the heptane has been metered in, the product slowly begins to crystallize in fine needles. After addition of heptane is complete, the viscous, but readily stirrable suspension is kept under reflux (110° to 112° C.) for a further hour.

After the suspension has cooled to 20° to 22° C., it is filtered off with suction and the suction filter material is washed first with 500 g of 1,2-dichlorobenzene/heptane (1:1) and then with 400 g of methanol.

The moist suction filter material (about 300 g) is dried at 65° to 70° C. in vacuo.

Yield: 146.5 g (about 98.5% (LC))→144.3 g (100%)= 60.5 % of theory, based on cyanuric chloride.

What is claimed is:

1. A process for the preparation of 2-(2,4-dihydroxyphenyl)-4,6-bis-(2,4-dimethylphenyl)-s-triazine of the formula I

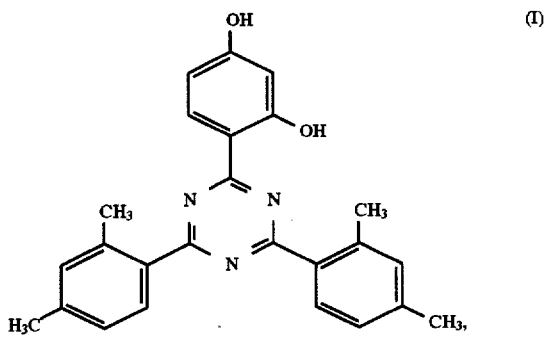

which comprises
a) reacting cyanuric chloride of the formula II

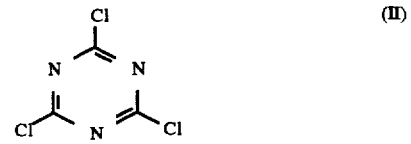

at a temperature of 0° to 110° C. in the presence of a Lewis acid in a ratio of 2.3 to 3.0 mol of Lewis acid per mole of cyanuric chloride employed in the presence of at least one inert chlorinated aromatic solvent, with 1,3-xylene of the formula III

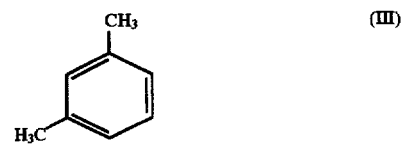

in a ratio of 2.1 to 2.5 mol of compound of the formula III per mole of cyanuric chloride employed with addition of compound of the formula III in a period of from 5 to 30 hours to give the compound of the formula IV

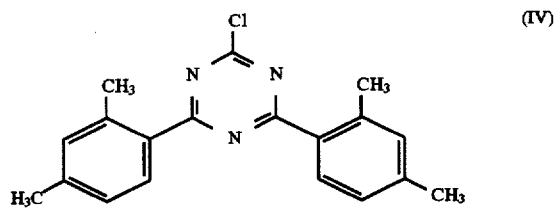

and then
b) without isolating the compound of the formula IV obtained reacting this with resorcinol in a ratio of 0.5 to 1.0 mol of resorcinol per mole of cyanuric chloride employed at a temperature from 0° to 100° C. to give the compound of the formula I.

2. A process according to claim 1, wherein in process step a) the compound of the formula III is added in 2 portions.

3. A process according to claim 2, wherein first 0.5 to 1.1 mol and then 2.0 to 1.0 mol of the compound of the formula III are added.

4. A process according to claim 2, wherein the addition of the first portion is carried out at 60° to 110° C., that of the second at 20° to 50° C.

5. A process according to claim 1, wherein in process step a) the addition of 0.5 to 1.1 mol of the compound of the formula III at 60° to 110° C. in the course of 2 to 12 hours, then the mixture is cooled to 20° to 50° C. in the course of 0 to 3 hours, after which the addition of 2.0 to 1.0 mol of the compound of the formula III takes place in the temperature range from 20° to 50° C. in the course of 5 to 15 hours.

6. A process according to claim 1, wherein in process step a) the addition of 0.85 to 1.0 mol of the compound of the formula III takes place at 83° to 87° C. in the course of 3.5 to 4.5 hours, then the mixture is cooled to 33° to 37° C. in the course of 1.4 to 1.6 hours, after which the addition of 1.45 to 1.3 mol of the compound of the formula III takes place in the temperature range from 33° to 37° C. in the course of 5.5 to 6.5 hours.

7. A process according to claim 1, wherein in process steps a) and b) the same chlorinated aromatic solvent is employed.

8. A process according to claim 7, wherein in process steps a) and b) chlorobenzene or dichlorobenzene are employed.

9. A process according to claim 1, wherein in process step a) the Lewis acid is employed in a ratio of 2.4 to 2.6 mol per mole of cyanuric chloride.

10. A process according to claim 9, wherein the Lewis acid is aluminium trichloride or aluminium tribromide.

11. A process according to claim 10, wherein the Lewis acid is aluminium trichloride.

12. A process according to claim 1, wherein in process step b) 0.7 to 0.8 mol of resorcinol are employed per mole of cyanuric chloride.

13. A process according to claim 1, wherein the temperature in process step b) is 35° to 80° C.

* * * * *